(12) United States Patent
Sundquist et al.

(10) Patent No.: US 10,962,521 B2
(45) Date of Patent: Mar. 30, 2021

(54) METHOD AND SYSTEM OF CONDITION MONITORING

(71) Applicant: Aktiebolaget SKF, Gothenburg (SE)

(72) Inventors: Fredrik Sundquist, Luleå (SE); Paer Marklund, Gammelstad (SE)

(73) Assignee: Aktiebolaget SKF, Gothenburg (SE)

( * ) Notice: Subject to any disclaimer, the term of this patent is extended or adjusted under 35 U.S.C. 154(b) by 372 days.

(21) Appl. No.: 15/895,479

(22) Filed: Feb. 13, 2018

(65) Prior Publication Data
US 2018/0238851 A1 Aug. 23, 2018

(30) Foreign Application Priority Data
Feb. 20, 2017 (GB) .................................... 1702678

(51) Int. Cl.
*G01N 33/28* (2006.01)
*G01M 13/04* (2019.01)
*G01N 27/06* (2006.01)

(52) U.S. Cl.
CPC ........ *G01N 33/2847* (2013.01); *G01M 13/04* (2013.01); *G01N 27/06* (2013.01)

(58) Field of Classification Search
CPC .... G01M 13/04; G01N 27/06; G01N 33/2847
See application file for complete search history.

(56) References Cited

U.S. PATENT DOCUMENTS

| 6,295,863 | B1 | 10/2001 | Ginder | |
|---|---|---|---|---|
| 8,943,911 | B1* | 2/2015 | Terrell | G01F 23/00 73/865.8 |
| 2010/0042389 | A1* | 2/2010 | Farruggia | G02B 27/0006 703/6 |
| 2015/0115983 | A1 | 4/2015 | Potyrailo | |
| 2017/0159716 | A1* | 6/2017 | Dittes | G01N 33/30 |

FOREIGN PATENT DOCUMENTS

| EP | 2952759 A1 | 12/2015 | |
|---|---|---|---|
| GB | 2536711 A | 9/2016 | |
| NL | 1017978 C2 | 11/2002 | |
| WO | 2014/094812 A1 | 6/2014 | |
| WO | WO-2014094812 A1 * | 6/2014 | ............ G01M 13/04 |

* cited by examiner

*Primary Examiner* — Son T Le
*Assistant Examiner* — Adam S Clarke
(74) *Attorney, Agent, or Firm* — Garcia-Zamor Intellectual Property Law; Ruy Garcia-Zamor; Bryan Peckjian

(57) ABSTRACT

A condition monitoring system that determines a presence of change of water content in grease. The system provides a sensor electrode that is placed in the space where the grease is located. The electrode is suitably a plate with a surface area creating a capacitance C. This in combination with a resistor R, creates an RC circuit. The system senses the RC circuit. The dielectric constant of the monitored grease varies in dependence of the water content of the grease. A change of the dielectric constant will change RC, that is then sensed by the system. An analysis of a change of RC will determine if there is a presence of a change of the level of water content in the monitored grease.

12 Claims, 4 Drawing Sheets

METHOD AND SYSTEM OF CONDITION MONITORING

CROSS-REFERENCE

This application claims priority to British patent application no. 1702678.2 filed on Feb. 20, 2017, the contents of which are fully incorporated herein by reference.

TECHNOLOGICAL FIELD

The invention concerns condition monitoring and is more particularly directed to detecting the presence of water in grease, especially in grease lubricated machine components such as rolling element bearings.

BACKGROUND

Reliable operation of rotating mechanical systems is highly dependent on proper lubrication. The condition of a lubricant is very important, especially for systems designed to operate for long periods with little or no maintenance. The presence of contaminants such as water or particles can lead to wear and damage of moving parts of the system and even premature catastrophic failure of the entire mechanical system. A lubricant of a mechanical system may primarily be either oil or grease based. Monitoring the condition of oil in an oil lubricated system can be accomplished by circulating the oil past a sensor and may additionally be provided with filters for removing contaminants. However, closed systems such as bearings are generally filled with an appropriate grease. The grease is maintained within the bearing or bearing housing with seals. The seals also protect the grease from ingress of contaminants such as water and particles. Seals may break or leak such that water enters the bearing or bearing housing. Water ingress decreases the lubrication ability of the grease and also increases the chance of corrosion damage of the bearing elements. There is thus a desire to monitor grease of a closed mechanical system, especially in relation to its water content. It is not possible to circulate the grease past a sensor without extreme difficulty and expense. There seems to still be room for improvements in this area.

SUMMARY

An object of the invention is to define a method and an apparatus of detecting a change of water content in grease, to thereby be able to monitor grease within a mechanical system.

The aforementioned object is achieved according to the invention by a condition monitoring system that determines a presence of change in a level of water content in grease. The system comprises a sensor unit and a analysis unit. The sensor unit generates an output signal relating to the level of water content of the monitored grease. The analysis unit determines in dependence of the output signal, the presence of a change of the level of water content in the monitored grease. According to the invention the sensor unit comprises a control unit, an electrically conducting electrode such as a plate, an output port that is controllable by the control unit, and an input port that is readably by the control unit. The electrically conductive sensor electrode is intended to be mounted in a space comprising grease to be monitored, such as for example in a bearing housing. The sensor electrode can for example be a plate of a suitable shape and geometry such as circular, square, rectangular, irregular, or any other shape with a surface area that may be flat or bent along one or more axes. The electrode can be a one centimeter diameter circle or a band encompassing partly or fully around for example a bearing. The controllable output port is coupled via a resistor to the electrode. The readable input port is directly coupled to the sensor electrode. The control unit toggles the output port between two different voltage levels, a high voltage level and a low voltage level. This is done in such a way that the output port is toggled to the opposite of the two voltage levels the control unit determines the input port to have. That is, if the control unit determines that the input port is at a low voltage level, then the control unit sets the output port to a high voltage level, and vice versa. The control unit additionally generates the output signal deriving it from the toggling of the output port, the state of the output port, a pulsed signal which will vary in frequency and cycle period in dependence of the water content of the grease. The output signal can be the pulsed signal directly, possibly buffered, a control signal from the control unit that toggles the output port, which can be a physical signal or just a software command to the output port, or the output signal is a representation of the pulsed signal or the control signal, all depending on how the further processing is done. The analysis unit comprises a frequency and/or cycle period determining unit and a comparison unit. The frequency and/or cycle period determining unit determines the frequency and/or the cycle period of the output signal. The cycle period being the inverse of the frequency. The comparison unit compares the currently determined frequency and/or cycle period of the output signal to a previously determined frequency and/or cycle period of the output signal and therefrom indicates if there is a presence of change of the level of water in the monitored grease or not.

Suitably the comparison unit determines that the water content is increasing when the frequency of the output signal decreases and/or the cycle period of the output signal increases.

Suitably the comparison unit determines that the water content is decreasing when the frequency of the output signal increases and/or the cycle period of the output signal decreases.

Suitably the comparison unit requires a predetermined frequency or cycle period difference between a currently determined frequency or cycle period, and a previously determined frequency or cycle period, within a predetermined time period before the difference is taken into account for determining if there is a change of level of water in the monitored grease or not.

Suitably frequency or cycle period difference peaks appearing during less than a predetermined time period are not taken into account for determining if there is a change of level of water in the monitored grease or not.

Advantageously the frequency determining unit determines an initial frequency and/or cycle period of the output signal as a calibration frequency and/or cycle period.

The different additional enhancements of the condition monitoring system according to the first embodiment of the invention can be combined in any desired manner as long as no conflicting features are combined.

The first embodiment is advantageous to implement as a retrofit to extend an existing condition monitoring system or in case of a new installation with a standard condition monitoring system comprising digital input and output ports. What is required is one free input port, one free output port and some (re-) programming of the system, in addition to one resistor and the sensor electrode.

The aforementioned object is also achieved according to the invention by a condition monitoring system to determine a presence of change in a level of water content in grease comprising a sensor unit and an analysis unit. The sensor unit generates an output signal relating to the level of water content of the monitored grease. The analysis unit determines in dependence of the output signal, the presence of change of the level of water content in the monitored grease. According to the invention the sensor unit comprises an electrically conductive sensor electrode, a first and a second port, and an RC oscillator unit. The sensor electrode can for example be a plate of a suitable shape and geometry such as circular, square, rectangular, irregular, or any other shape with a surface area that may be flat or bent along one or more axes. The electrode can be a one centimeter diameter circle or a band encompassing partly or fully around for example a bearing. The electrically conductive sensor electrode is intended to be mounted in a space comprising grease to be monitored. The first port is coupled via a resistor to the sensor electrode. The second port is directly coupled to the sensor electrode. The sensor electrode and the resistor makes up the RC part of the RC oscillator unit, and the rest of the oscillator is coupled to the first and second port. The oscillator unit generates the output signal. The analysis unit comprises a frequency and/or cycle period determining unit and a comparison unit. The frequency and/or cycle period determining unit determines the frequency and/or the cycle period of the output signal. The comparison unit compares the currently determined frequency and/or cycle period of the output signal to a previously determined frequency and/or cycle period of the output signal and therefrom indicates if there is a presence of change of the level of water in the monitored grease or not.

Suitably the comparison unit determines that the water content is increasing when the frequency of the output signal decreases and/or the cycle period of the output signal increases.

Suitably the comparison unit determines that the water content is decreasing when the frequency of the output signal increases and/or the cycle period of the output signal decreases.

Suitably the comparison unit requires a predetermined frequency or cycle period difference between a currently determined frequency or cycle period, and a previously determined frequency or cycle period, within a predetermined time period before the difference is taken into account for determining if there is a change of level of water in the monitored grease or not.

Suitably frequency or cycle period difference peaks appearing during less than a predetermined time period are not taken into account for determining if there is a change of level of water in the monitored grease or not.

Advantageously the frequency determining unit determines an initial frequency and/or cycle period of the output signal as a calibration frequency and/or cycle period.

The different additional enhancements of the condition monitoring system according to the second embodiment of the invention can be combined in any desired manner as long as no conflicting features are combined.

The aforementioned object is further achieved according to the invention by a condition monitoring system that determines a presence of change of water content in grease. The system comprises a sensor electrode that is placed in the space where the grease is located. The electrode is suitably a plate with a surface area creating a capacitance C. This in combination with a resistor R, creates an RC circuit. The system senses the RC circuit. The dielectric constant of the monitored grease varies in dependence of the water content of the grease. A change of the dielectric constant will change RC, that is then sensed by the system. An analysis of a change of RC will determine if there is a presence of a change of the level of water content in the monitored grease.

Solutions with sensors that measure electrical properties of a lubricant (e.g. capacitance and/or inductance) could also be considered. These would however best be suited for oil lubricated systems where the lubricant can be pumped to the sensor. The installation of these sensors would however be quite expensive and, more importantly, could normally not be successfully used in grease lubricated components.

The key with the proposed method and apparatus is the simplicity, which will lead to a low cost and easy installation. The proposed measurement technique with digital measurement ports is also robust and non-sensitive to disturbances during measurement.

In order to be installed in a large scale in industry, sensors need to be cheap, reliable, robust and easy to install and also to replace if necessary. These properties are often of much higher importance than the maximum possible resolution of the measured values. In e.g. the case of water detection in grease lubricated bearings the most important need in industry is to easily detect a high water content, e.g. in many cases due to a broken/leaking seal that will lead to a rapid bearing failure, compared to accurately measure a small water content which is only harmful for the bearing in the long run. The proposed sensor technique fulfils all above demands and is also easy to use with communication to existing SKF IMx® hard-/software or other condition monitoring equipment. This makes it easy to install with low cost in existing SKF or other branded systems and could still solve the most important problem; to detect when the water content is dangerously high and the grease needs to be changed and the seal might need to be inspected and/or replaced.

Other advantages of this invention will become apparent from the detailed description.

BRIEF DESCRIPTION OF THE DRAWINGS

The invention will now be described in more detail for explanatory, and in no sense limiting, purposes, with reference to the following figures, in which.

DETAILED DESCRIPTION

In order to clarify the method and device according to the invention, some examples of its use will now be described in connection with FIGS. 1 to 4.

Figure 1:
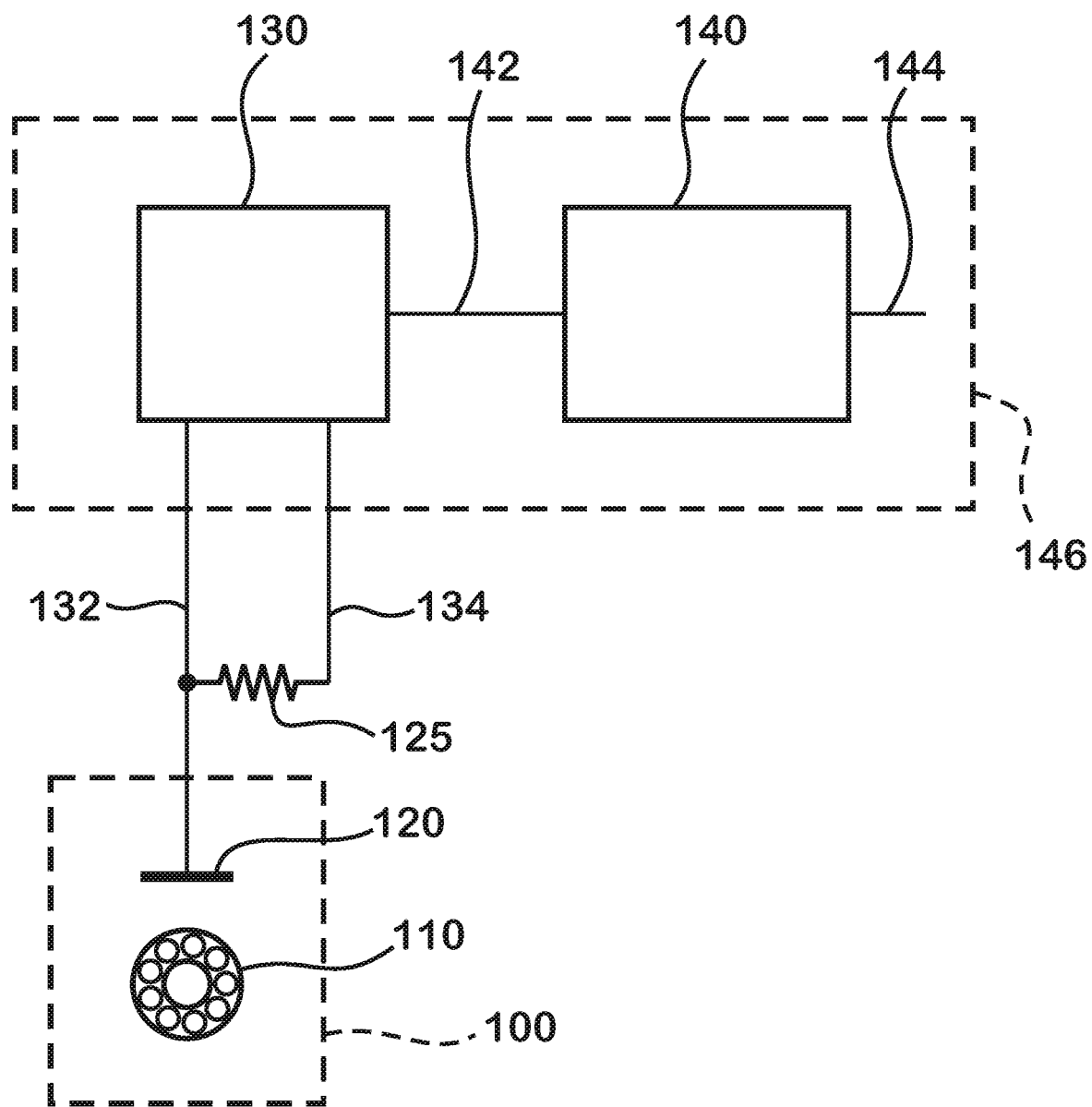
FIG. 1 illustrates an condition monitoring system according to the invention

FIG. 1 illustrates a condition monitoring system 146 according to the invention being part of an existing condition monitoring system or dedicated water in grease condition monitoring system. The system comprises an electrically conductive sensor electrode 120 such as a plate of a suitable shape and geometry, a charging/discharging resistor 125, an analysis unit 140, a control unit 130 with a signal output 142 to the analysis unit 140, an input port 132 coupled to the sensor electrode, an output port 134 coupled to the sensor electrode 120 through the charging/discharging resistor 125, and suitably an analysis output 144. The sensor electrode 120 is intended to be mounted in proximity to a lubricant, grease, such as within a rolling element bearing housing 100 of a rolling element bearing 110, such that the lubricant acts a dielectric for the sensor electrode 120.

The invention is based on the basic inventive idea of the dielectric constant and conductivity of grease changes with its water content, and in case the grease creates a bridge between the sensor electrode 120 and something that is earthed, then also that the impedance of grease changes in relation to its water content plays a role.

According to a first embodiment of the invention, the control unit 130 toggles an output voltage of the output port 134 in dependence of a determined voltage of the input port 132. The output voltage is toggled between a high output voltage, such as 5 volts, and a low output voltage, such as 0 volts. The control unit 130 will determine that there is a high voltage, such as 5 volts, at the input port 132, if the voltage present at the input port 132 is equal to or higher than a first predetermined voltage, such as 3.6 volts. In addition the control unit 130 will determine that there is a low voltage, such as 0 volts, at the input port 132, if the voltage present at the input port 132 is equal to or lower than a second predetermined voltage, such as 0.8 volts. The control unit 130 will keep the output voltage of the output port 134 the opposite of the determined voltage of the input port 132. The output port 134 will thus charge and discharge the sensor electrode 120 through the charging/discharging resistor 125. The sensor electrode 120 will represent a capacitance C in relation to the dielectric constant of the grease, creating an RC circuit that will vary in dependence of the dielectric constant (relative permittivity) around the sensor electrode 120. The resistor 125 has to be chosen in relation to the size and placement of the sensor electrode 120 and in relation to desired RC values giving desirable dry grease and wet grease values of the output 142. A suitable value to start with could for example be 1 M Ohm for the charging/discharging resistor 125. If the output port 134 is set to a high output voltage, then the voltage level at the input port 132 will rise from the second predetermined voltage until it reaches the first predetermined voltage. This will cause the control unit 130 to set the output port 134 to a low voltage output, then the voltage level at the input port 132 will fall from the first predetermined voltage to the second predetermined voltage. The rise and fall times are dependent on the value of R, the resistor 125, and C, the sensor electrode 120, being influenced by the dielectric constant of the grease. The combined times it takes the voltage level at the input port to rise and fall will define the cycle period (the inverse of frequency) that will indicate the wetness of the grease. If a calibration measurement is taken of dry grease and possibly one or more to define how the rate of change of cycle period/frequency relates to water content, then the absolute value of water content/percentage in grease can be determined.

In a second embodiment of the invention the control unit 130 is an RC-oscillator where the resistor 125 and the sensor electrode 120 form the oscillator's RC circuit.

The output signal 142 will for the second embodiment suitably be the output of the oscillator, having a frequency with a corresponding cycle period that will represent and vary with the water content of the grease. For the first embodiment the output signal 142 can be the voltage present at the output port 134, or transformed to a software variable that represent the frequency and/or the cycle period, or a scaled version of one or both of these, by for example a control signal that the control unit uses to control the output port, this can be a physical signal or a command. This depends if the processing and comparison is done directly in hardware or in software on a computer. The output signal 142 will enter the analysis unit 140 that suitably comprises a determining unit and a comparison unit. The determining unit will determine the frequency and/or cycle period of the output signal. This is saved as a currently determined frequency and/or cycle period. The comparison unit will then compare the currently determined frequency and/or cycle period with a previously determined one or more. By this comparison and possibly further analysis it is determined if there is a change in the amount of water in the monitored grease. The comparison unit will then output an analysis output 144 that can be used by other parts of the condition monitoring system, to for example create an alarm.

Figure 2:
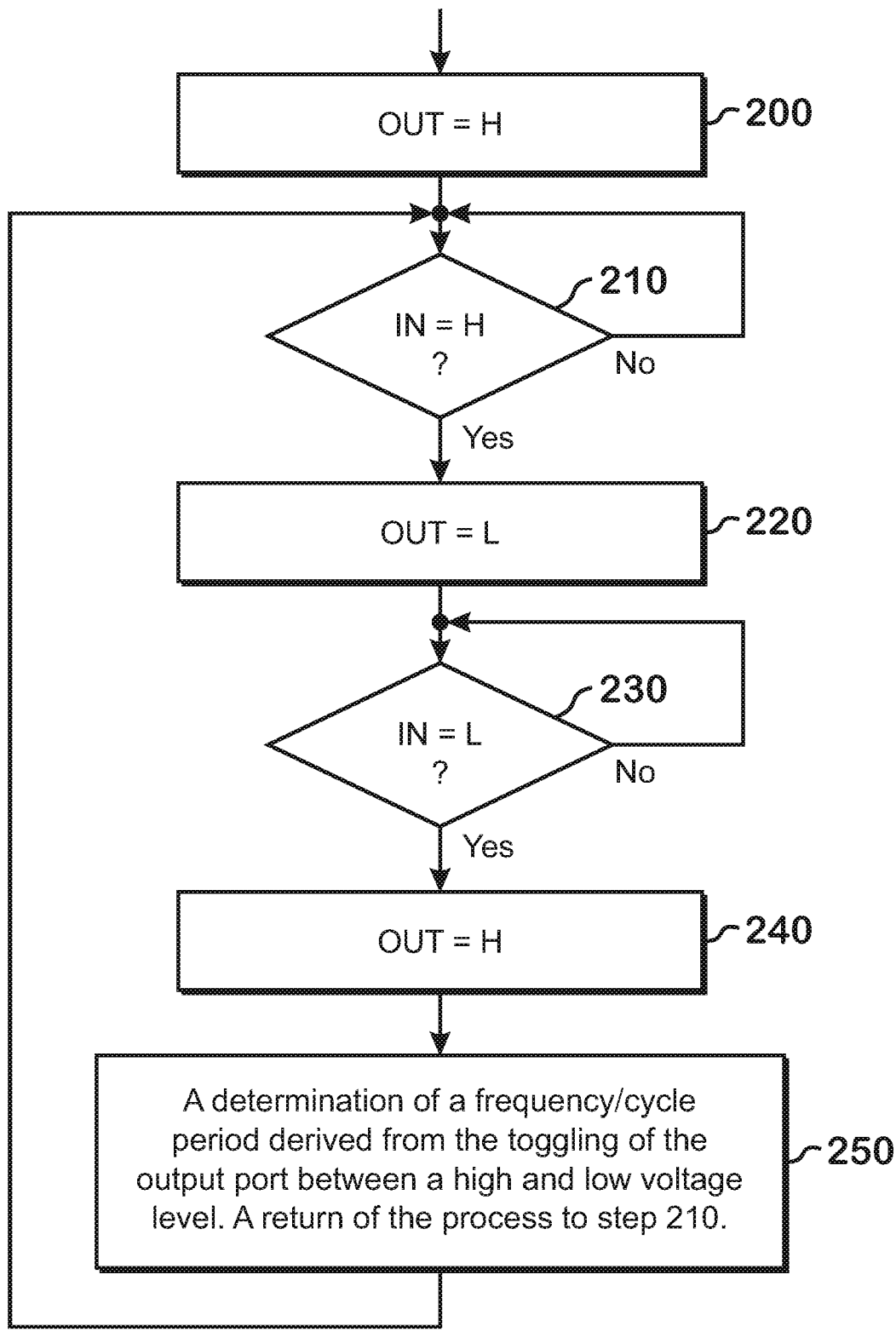
FIG. 2 illustrates a flowchart of the frequency determination unit according to the invention

FIG. 2 illustrates a flowchart of the control unit according to the first embodiment of the invention. In a first step 200 the output port is set to a high voltage level. In a second step 210 a test is made to see if the input port is determined to have a high voltage level or not, if it does not, then the process continues the testing at the second step 210. When it is determined that the voltage level at the input port is at a high voltage level then the process continues with a third step 220 that will set the output port to a low voltage output level. Then in a fourth step 230 it is tested to see if the input port is determined be at a low voltage level or not, if it does not, then the process continues the testing at the fourth step 230. When it is determined that the voltage level at the input port is a low voltage level then the process continues with a fifth step 240 where the output port is set to a high voltage level. Thereafter in a sixth step 250 a frequency or a cycle period of toggling the output port between a high and low voltage level is determined, then the process returns to the second step 210.

Figure 3:
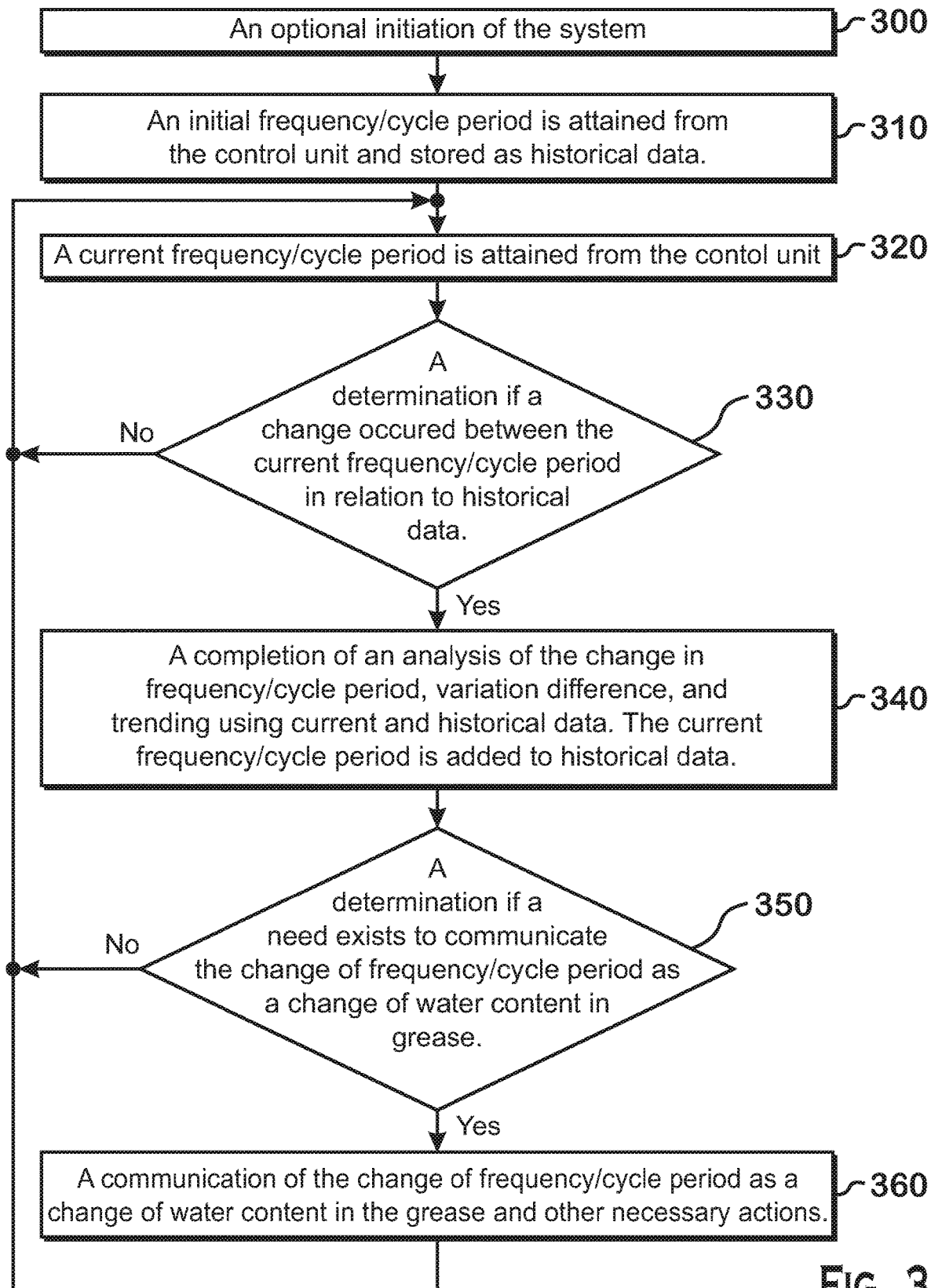
FIG. 3 illustrates a flowchart of the analysis unit according to the invention.

FIG. 3 illustrates a flowchart of the analysis unit according to the invention. In a suitable optional step 300 there is an initiation of the system such as resetting variables etc. The optional step may include a calibration part, wherein one or more frequency/cycle period measurements are taken of grease with a known water content. A calibration enables an absolute value of the water content in the grease to be given. Thereafter in a first step 310, an initial frequency/cycle period is attained from the control unit. Store the initial frequency/cycle period as historical data. Then in a second step 320 a current frequency/cycle period is attained from the control unit. In a third step 330 it is determined if there is a change in frequency/cycle period between the current frequency/cycle period in relation to historical data, if not then return to 320. If it is determined that there is a change, the process continues with a fourth step 340 that analyzes the change of frequency/cycle period, variation difference, trending, using current and historical data. The current frequency/cycle period is added to the historical data. In a fifth step 350 it is determined if there is a need to communicate the change of frequency/cycle period as a change of water content in the grease, if not then return to 320. In a sixth step 360 communicate the change and other necessary actions, then return to 320.

Figure 4:
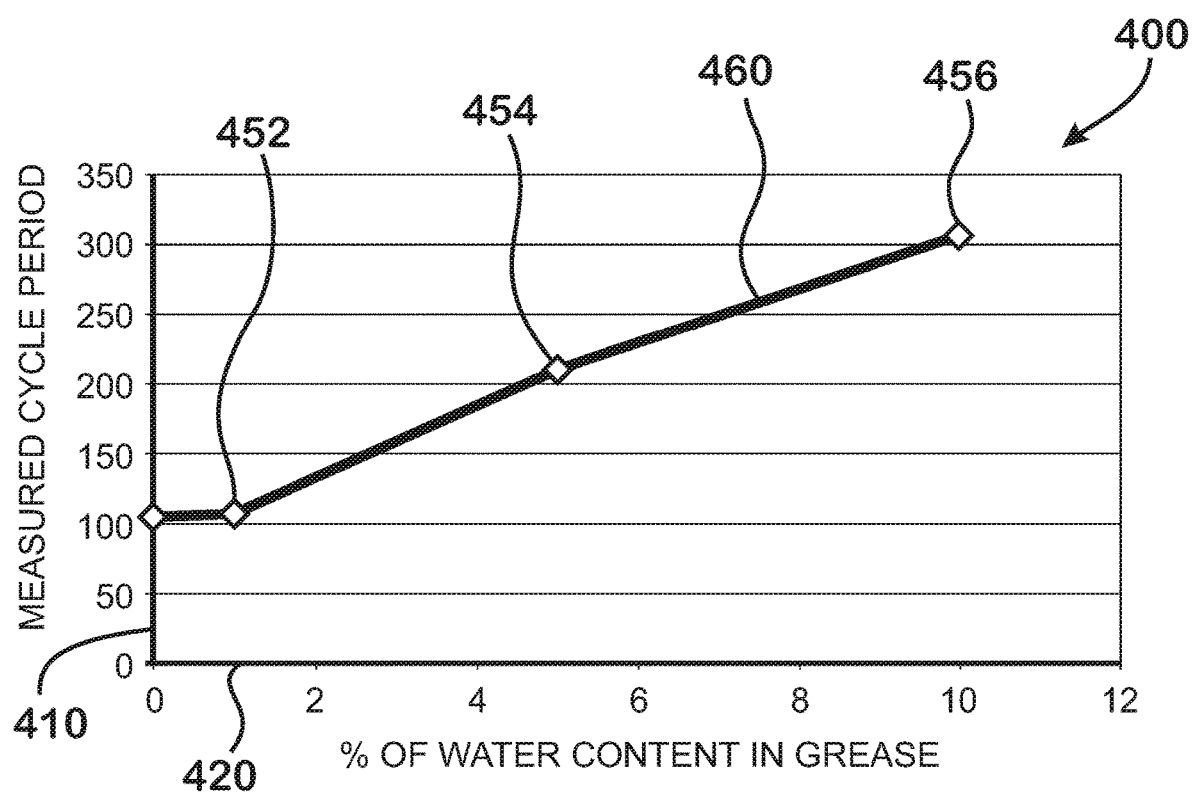
FIG. 4 illustrates an example of cycle period measurement/generation in relation to grease water content.

FIG. 4 illustrates an example of cycle period measurement/generation in relation to grease water content. A chart 400 shows a relationship between measured/generated cycle period and water in grease content where the Y-axis 410, is measured cycle period, illustrated cycle periods are just scaled examples and will depend on application and parameters such as measuring apparatus, grease type, geometry, size and location of sensor electrode, geometry and size of housing. The X-axis 420 is the % of water content in a grease. A few points are illustrated in the chart 400. Initial measured/generated cycle period 452 and up to about 1% of water content, a cycle period 454 showing 5% water content, a cycle period 456 showing 10% water content. A curve fitting 460 has also been done, showing a relatively linear relationship between water content and measured/generated cycle period.

The invention is not restricted to the above-described embodiments, but may be varied within the scope of the following claims.

REFERENCE NUMBERS

100 Rolling element housing,
110 Rolling element bearing,
120 Sensor electrode, such as a plate,
125 Charging and discharging resistor,
130 Control unit,
132 Input from sensor electrode,
134 Output to sensor electrode,
140 Analysis unit,
142 Signal output from control unit to analysis unit,
144 Analysis output
146 Condition monitoring system being part of an existing condition monitoring system or dedicated water in grease condition monitoring system.
200 Output is set to a high output level,
210 Test to see if input is considered high or not, if not then continue testing,
220 Output is set to a low output level,
230 Test to see if input is considered low or not, if not then continue testing,
240 Output is set to a high output level,
250 Frequency and/or cycle period of toggling output high/low is determined, then return to 210.
300 Initiation of the system such as resetting variables etc.,
310 An initial frequency is attained from the frequency output of the control unit,
320 A current frequency is attained from the frequency output of the control unit,
330 Is there a change in frequency between the current frequency and the initial frequency, if not then return to 320,
340 Analyze the change of frequency, variation difference, trending,
350 Determine if there is need to communicate the change of frequency, if not then return to 320,
360 Communicate change and other necessary actions, then return to 320.
400 Chart showing relationship between measured/generated cycle period and water in grease content,
410 Y-axis, measured period, illustrated periods are just an example and will depend on application and parameters such as measuring apparatus, grease type, geometry, size and location of sensor plate, geometry and size of housing,
420 X-axis, % of water content in grease,
452 Initial measured/generated cycle period and up to about 1% of water content,
454 Cycle period at 5% water content,
456 Cycle period at 10% water content,
460 Curve fitting, showing a linear relationship between water content and measured/generated cycle period.

What is claimed is:

1. A condition monitoring system to determine a presence of change in a level of water content in grease comprising:
    a sensor unit generating an output signal relating to the level of water content of the monitored grease;
    an analysis unit determining in dependence of the output signal, the presence of change of the level of water content in the monitored grease;
    the sensor unit comprises:
    an electrically conductive sensor electrode intended to be mounted in a space comprising grease to be monitored;
    an output port coupled via a resistor to the sensor electrode;
    an input port directly coupled to the sensor electrode;
    a control unit that toggles the output port between two different voltage levels, a high voltage level and a low voltage level, in such a way that the output port is toggled to the opposite of the two voltage levels the control unit determines the input port to have, wherein the output port maintains the high voltage level until the input port measures a same high voltage level, when the input port measures the same high voltage level as the output port the output port changes to provide the low voltage level and maintains the low voltage level until the input port measures a same low voltage level, when the input port measures the same low voltage level as the output port the output port changes to provide the high voltage level, wherein the control unit additionally generates the output signal deriving it from the toggling of the output port; and
    the analysis unit comprises:
    a determining unit that determines a frequency and/or a cycle period of the output signal;
    a comparison unit that compares the currently determined frequency and/or cycle period of the output signal to a previously determined frequency and/or cycle period of the output signal and therefrom indicates if there is a presence of change of the level of water in the monitored grease or not.

2. The condition monitoring system according to claim 1, characterized in that the comparison unit determines that the water content is increasing when the frequency of the output signal decreases and/or the cycle period of the output signal increases.

3. The condition monitoring system according to claim 1, wherein the comparison unit determines that the water content is decreasing when the frequency of the output signal increases and/or the cycle period of the output signal decreases.

4. The condition monitoring system according to claim 1, wherein the comparison unit requires a predetermined frequency and/or cycle period difference within a predetermined time period before the difference is taken into account.

5. The condition monitoring system according to claim 1, wherein frequency and/or cycle period difference peaks appearing during less than a predetermined time period are not taken into account.

6. The condition monitoring system according to claim 1, wherein the determining unit determines an initial frequency and/or cycle period of the output signal as a calibration frequency and/or calibration cycle period.

7. A condition monitoring system to determine a presence of change in a level of water content in grease comprising:
    a sensor unit generating an output signal relating to the level of water content of the monitored grease;
    an analysis unit determining in dependence of the output signal, the presence of change of the level of water content in the monitored grease; wherein the sensor unit comprises:

an electrically conductive sensor plate intended to be mounted in a space comprising grease to be monitored;

a first port coupled via a resistor to the sensor plate; a second port directly coupled to the sensor plate;

an RC oscillator unit, where the sensor plate and the resistor makes up the RC part and that the rest of the oscillator is coupled to the first and second port, where the oscillator unit generates the output signal;

and in that the analysis unit comprises:

a determining unit that determines a frequency and/or cycle period of the output signal; and a comparison unit that compares the currently determined frequency and/or cycle period of the output signal to a previously determined frequency and/or cycle period of the output signal and therefrom indicates if there is a presence of change of the level of water in the monitored grease or not.

8. The condition monitoring system according to claim 7, wherein the comparison unit determines that the water content is increasing when the frequency of the output signal decreases and/or the cycle period of the output signal increases.

9. The condition monitoring system according to claim 7, wherein the comparison unit determines that the water content is decreasing when the frequency of the output signal increases and/or the cycle period of the output signal decreases.

10. The condition monitoring system according to claim 7, wherein the comparison unit requires a predetermined frequency and/or cycle period difference within a predetermined time period before the difference is taken into account.

11. The condition monitoring system according to claim 7, wherein frequency and/or cycle period difference peaks appearing during less than a predetermined time period are not taken into account.

12. The condition monitoring system according to claim 7, wherein the determining unit determines an initial frequency and/or cycle period of the output signal as a calibration frequency and/or calibration cycle period.

* * * * *